US012508404B2

(12) United States Patent
Cresswell

(10) Patent No.: US 12,508,404 B2
(45) Date of Patent: Dec. 30, 2025

(54) SHEATH SPLITTING APPARATUS

(71) Applicant: Vascutek Limited, Renfrewshire (GB)

(72) Inventor: Callum Cresswell, Renfrewshire (GB)

(73) Assignee: Vascutek Limited, Renfrewshire (GB)

(*) Notice: Subject to any disclaimer, the term of this patent is extended or adjusted under 35 U.S.C. 154(b) by 1113 days.

(21) Appl. No.: 17/439,687

(22) PCT Filed: Mar. 25, 2020

(86) PCT No.: PCT/GB2020/050799
§ 371 (c)(1),
(2) Date: Sep. 15, 2021

(87) PCT Pub. No.: WO2020/193975
PCT Pub. Date: Oct. 1, 2020

(65) Prior Publication Data

US 2022/0161004 A1 May 26, 2022

(30) Foreign Application Priority Data

Mar. 25, 2019 (GB) .................................... 1904073

(51) Int. Cl.
*A61M 25/06* (2006.01)
*A61B 17/12* (2006.01)

(52) U.S. Cl.
CPC .................... *A61M 25/0668* (2013.01); *A61B 2017/12004* (2013.01); *A61B 2017/12054* (2013.01); *A61B 17/12131* (2013.01); *A61M 2025/0675* (2013.01)

(58) Field of Classification Search
CPC ....... A61M 25/0668; A61M 2025/0675; A61F 2/97
See application file for complete search history.

(56) References Cited

U.S. PATENT DOCUMENTS

| | | | | |
|---|---|---|---|---|
| 6,497,681 B1* | 12/2002 | Brenner ............ | A61M 25/0668 604/524 |
| 2010/0298839 A1* | 11/2010 | Castro ................ | A61B 17/3421 604/164.05 |
| 2013/0053780 A1* | 2/2013 | Goode ............... | A61B 17/3468 604/164.05 |

(Continued)

FOREIGN PATENT DOCUMENTS

EP 3042686 A1 7/2016

OTHER PUBLICATIONS

International Search Report and Written Opinion for International Application No. PCT/GB2020/050799 dated Jul. 14, 2020.

*Primary Examiner* — Martin T Ton
(74) *Attorney, Agent, or Firm* — Stephen J. Kenny; Emily H. Yasharpour; Foley Hoag LLP

(57) ABSTRACT

The present invention concerns a sheath splitting apparatus for use with a medical device delivery system for deploying a sheathed medical device. The sheath splitting apparatus comprising: a body 3 having a medical device pathway 11 for receiving a medical device, and one or more arm members having one or more guide elements 12 defining a sheath pathway for guiding sheath material removed from the sheathed medical device. At least a section of the one or more arm members is movable towards and away from the longitudinal axis of the medical device pathway.

22 Claims, 9 Drawing Sheets

(56) References Cited

U.S. PATENT DOCUMENTS

Figure 1:
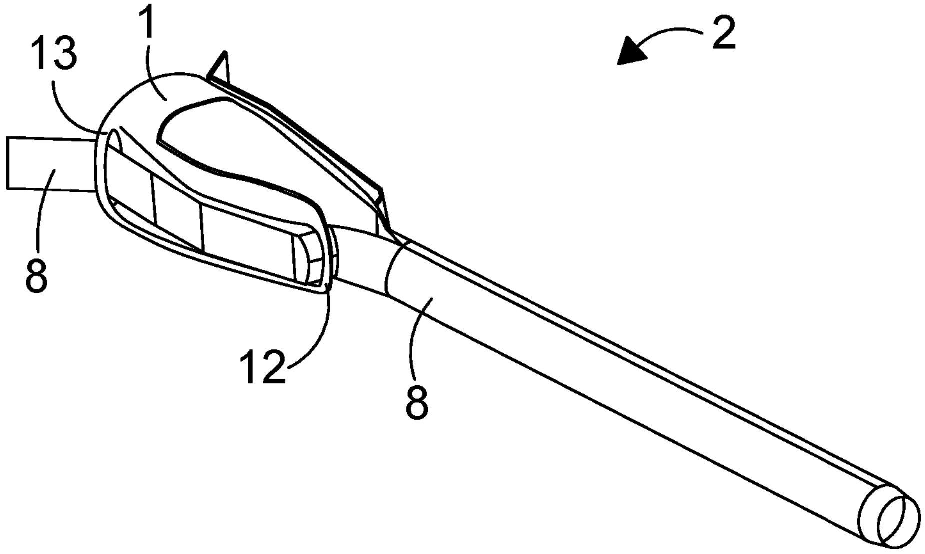

| | | | | |
|---|---|---|---|---|
| 2013/0184805 | A1* | 7/2013 | Sawada ............ | A61M 25/0097 623/1.11 |
| 2015/0231369 | A1 | 8/2015 | Gray et al. | |
| 2020/0306506 | A1* | 10/2020 | O'Carrol ........... | A61M 25/0668 |

* cited by examiner

SHEATH SPLITTING APPARATUS

RELATED APPLICATIONS

This application is the U.S. National Stage application for International Application No.: PCT/GB2020/050799, filed Mar. 25, 2020, which claims priority to Great Britain Application No.: 1904073.2, filed Mar. 25, 2019, the relevant teachings of each of which are incorporated by reference in their entirety The present invention relates to an apparatus and a method for use in vascular surgery and in particular, though not exclusively, to a sheath splitting apparatus and its method of use in endovascular aneurysm repair.

In this regard, in the context of on-pump procedures, fully open repair, such as the Crawford procedure, is known to be associated with high mortality/morbidity and post-operative complications. Furthermore, hybrid repair, such as visceral debranching followed by a stent grafting/Octopus procedure, cannot be carried out on a large cohort of patients, for example that have connective tissue disorders. Moreover, fully endovascular and hybrid repair both require good access for the endovascular device, which can similarly be problematic with a large cohort of patients.

In general, on-pump procedures using Cardiopulmonary Bypass (CPB) machinery, are known to be associated with increased risks of shock/haemorrhage, neurologic, cardiac, respiratory, renal, acute renal failure, adult respiratory distress syndrome, implant infection, postoperative infection, septicaemia, pneumonia, and peripheral vascular complications, compared with off-pump procedures Evidence suggests that off-pump surgery has advantages as it appears to reduce mortality and respiratory complications, shorten lengths-of-stay, and increases discharges directly home.

There is as such an unmet need for implanting a thoracoabdominal medical device off-pump, namely without the use pulmonary bypass machinery.

An object of the present invention is therefore to provide an apparatus and method which seek to address the issues identified above.

According to the present invention there is provided sheath splitting apparatus for use with a medical device delivery system for deploying a sheathed medical device; the sheath splitting apparatus comprising:—a body having a medical device pathway for receiving a medical device, and one or more arm members having one or more guide elements defining a sheath pathway for guiding sheath material from the sheathed medical device; wherein at least a section of the one or more arm members is movable towards and away from the longitudinal axis of the medical device pathway. In this way, the apparatus affords an improved mechanism for assisting in deploying a medical device.

Preferably, two arm members are provided, each with one or more guide elements for guiding sheath material. With two such arm members, sheath material removed from the medical device is split into two tails which respectively follow sheath pathways on opposing exterior sides of the apparatus.

Preferably, at least a section of each arm member is formed of resiliently deformable material. The arm member material may in this regard be profiled to enhance said movement.

Conveniently, at least a section of each arm member is hingeably mounted. Each arm member may moreover have a mechanical, articulated joint.

Conveniently, each arm member is configured to deflect radially inwardly under the action of sheath material being pulled along the sheath pathway, thus facilitating the splitting process.

Preferably, a proximal end of each arm member naturally extends to a position radially outwardly from a medical device within the apparatus.

Conveniently, each arm member is configured at its proximal end to present a profile accommodating outward deflection of the arm member on distally directed fluid flow through a medical device present in the apparatus. In this manner, the risk of damage caused by each arm member as blood flows through the medical device is mitigated. To this end, each arm member preferably has an outwardly splayed profile at its proximal end. The arm members may in this respect be curved at their proximal end to match the substantially circular profile of the sheath.

Conveniently, each arm extends longitudinally, substantially parallel with the axis of the medical device pathway and has a first guide element at a proximal extent thereof.

Preferably, the sheath pathway comprises a second guide element, provided distally of the first guide element and circumferentially aligned with the first guide element.

Conveniently, the first and second guide elements are provided either side of a hinge point of each arm member.

Preferably, the one or more guide elements are slots in the arm member. Conveniently, the slots are open slots.

Preferably, the sheath pathway extends from inside each arm member, through a first guide element to the exterior of the arm member, along the exterior of the arm member and through the second guide member provided distally of the first guide element.

Conveniently, the exterior profile of each arm member is raised, radially outwardly, to present a pressure point. This can be acted upon by sheath material when tensioned as it is removed from the medical device, thereby assisting in deflecting the arm member radially inwardly.

Preferably, the body has clamping means for reducing the cross-sectional area of at least part of the medical device pathway. Conveniently, the body comprises a plurality of body sections couplable together for housing around said medical device to be delivered.

Preferably, said body has two body sections that are hingeably couplable.

Conveniently, the clamping means takes the form of a clamp profile provided on each body section, the clamp profiles of the body sections inter-engaging on coupling of the body sections for compressing the material of a medical device provided in the apparatus.

Preferably, the clamp profile on each body section is tooth-like, and defines a central aperture when the body sections are coupled, the central aperture being dimensioned for compressing the medical device sufficiently against a delivery shaft to prevent blood leakage there-between, but loose enough to allow the delivery shaft to slide within the medical device.

Conveniently, the clamp profile on one body section has a single tooth profile and the inter-engaging profile on the other body section has a pair of tooth profiles, that slidably interlock either side of the single tooth profile when the body sections are coupled together.

According to a further aspect of the present invention there is provided a method of removing a sheath from a medical device, using the sheath splitting apparatus defined above, the method comprising the steps:—inserting the sheathed medical device into a vessel, with clamping means of the apparatus compressing onto the medical device to create a seal preventing blood leakage between a delivery shaft and the medical device; pulling on the sheath material tails from the distal end of the apparatus, the or each arm member consequently deflecting radially inwardly, closer to alignment with the medical device outer profile; removing the sheath from the device so that the device expands radially outwardly to engage the vessel; and allowing blood flow through the medical device, the blood flow forcing the or each arm to deflect radially outwardly. In this way, each arm deflects in a controlled fashion, thereby preventing it from restricting the size of the device. Whilst the clamping means prevents blood leakage between the delivery shaft and the medical device, blood can flow through other parts or branches of the device.

According to a further aspect of the present invention there is provided a medical device delivery system for deploying a sheathed medical device, the system comprising:—a medical device delivery shaft for holding a deployable medical device; a sheathed medical device provided on said delivery shaft; and a sheath splitting apparatus comprising a body having a medical device pathway for receiving said medical device provided on said delivery shaft, the sheath splitter apparatus comprising one or more arm members having one or more guide elements defining a sheath pathway for guiding sheath material removed from the sheathed medical device; wherein the one or more arm members are movable towards and away from the longitudinal axis of the medical device pathway.

Conveniently, each arm member is configured to deflect radially inwardly on sheath removal towards said delivery shaft and then radially outwardly post sheath removal.

Preferably, the sheath splitter apparatus comprises clamping means configured to compress the medical device against the delivery shaft to prevent blood leakage.

Certain embodiments of the present invention will now be described, by way of example and with reference to the accompanying drawings of which:—

Figure 2A:
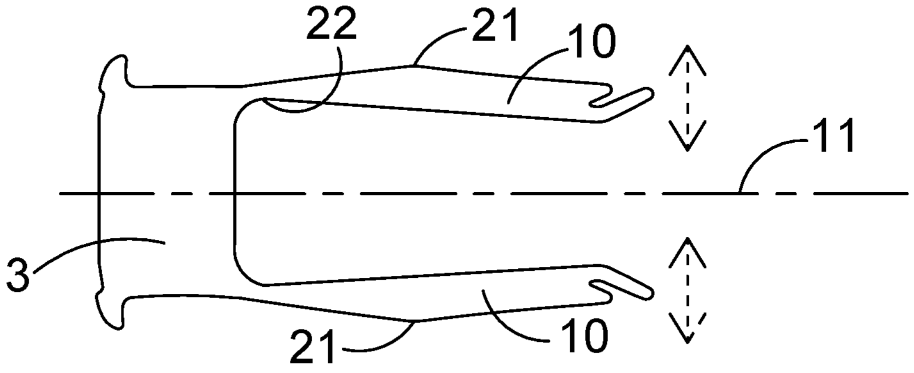
Figure 2B:
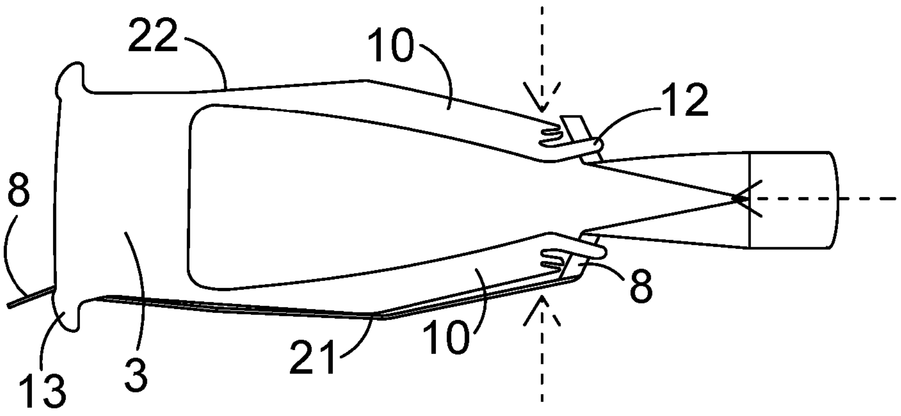
Figure 3:
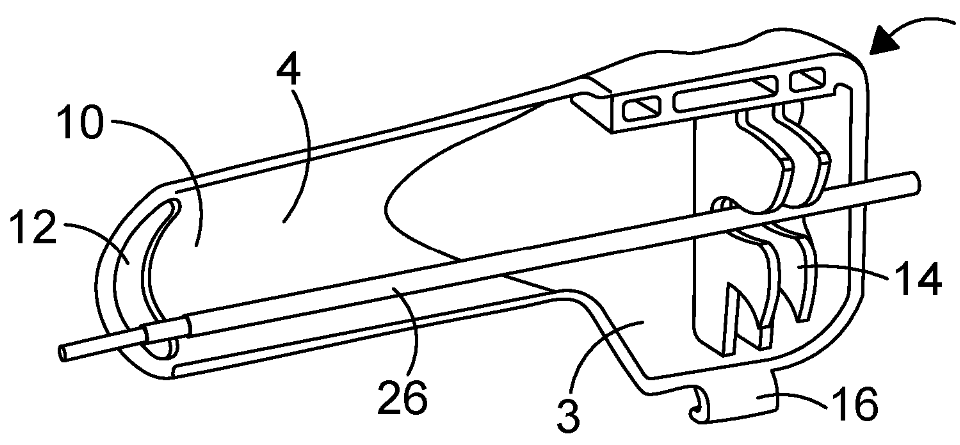
Figure 4A:
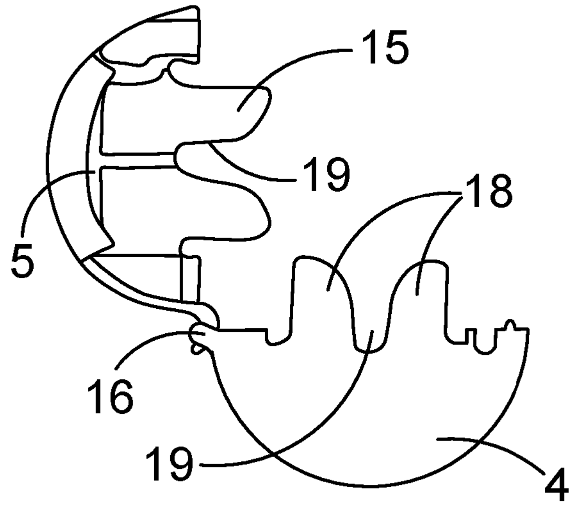
Figure 4B:
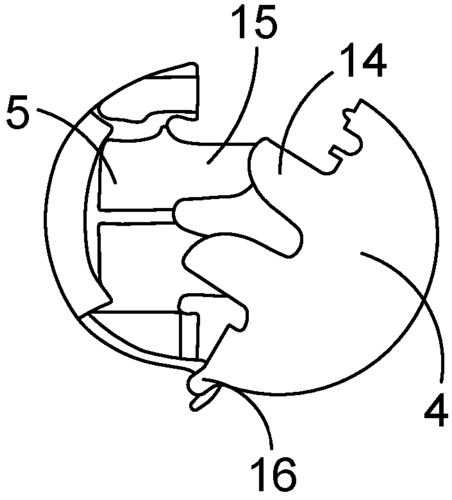
Figure 4C:
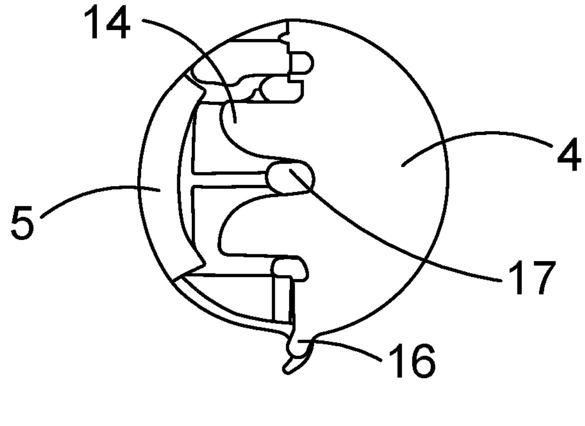
Figure 9:
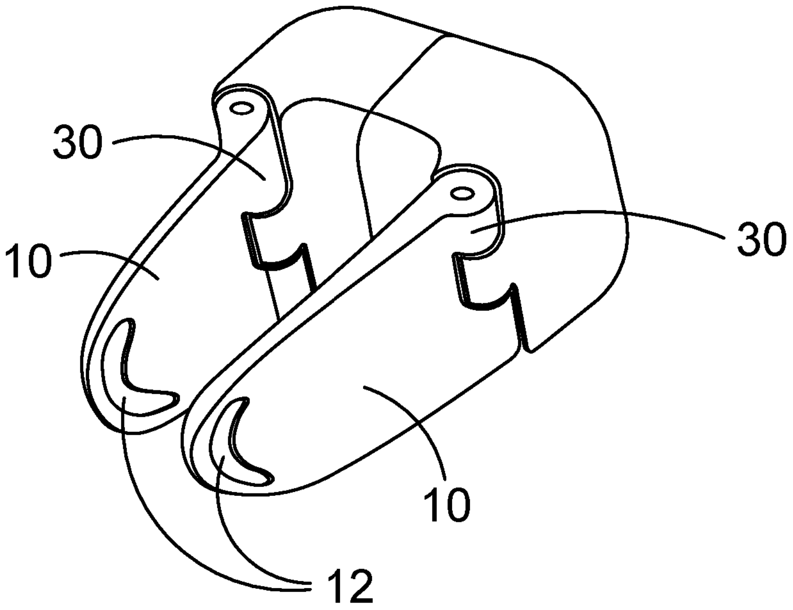
Figure 10:
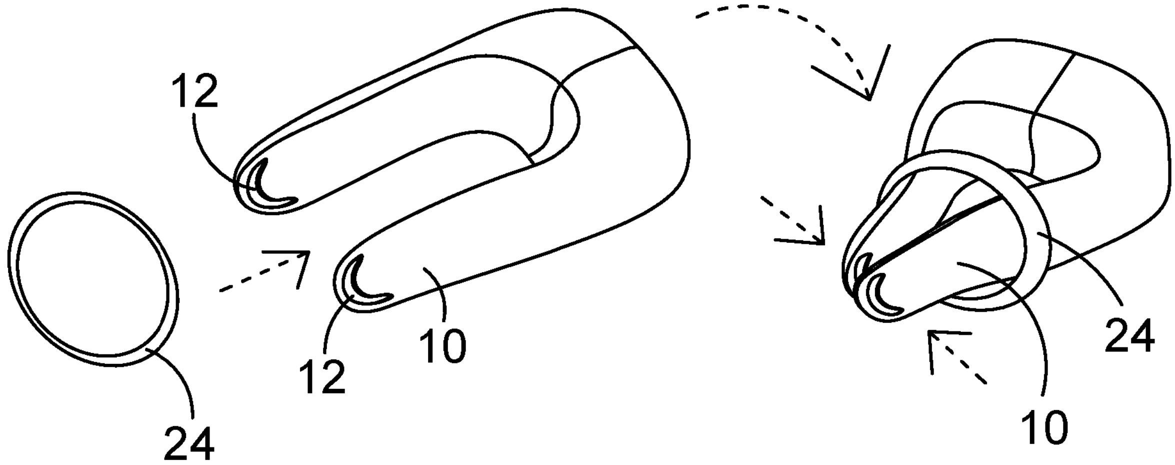

FIG. 1 shows a view of a sheath splitting apparatus according to the present invention;

FIGS. 2*a* and 2*b* show operation of arm members of the present invention;

FIG. 3 shows an internal view of the apparatus of FIG. 1 with an additional delivery shaft member positioned through the centre of the apparatus;

FIGS. 4*a* to 4*c* show stages of clamping operation of a clamping means of the apparatus;

FIGS. 5*a*, 5*b*, 6*a*, 6*b* and 7 show stages of operation of the apparatus of the present invention with a medical device;

FIGS. 8*a* to 8*f* show the stages of use of the present invention in implanting a thorocoabominal device;

FIG. 9 shows a further embodiment of arm members of the present invention; and FIG. 10 shows an additional embodiment of the present invention.

As shown in the Figures, a sheath splitting apparatus 1 of the present invention is provided as part of a medical device delivery system 2.

In a preferred form, the sheath splitter apparatus comprises a body 3, having a pair of opposing sides 4, 5 that are couplable together to define a central pathway for a medical device 6 there-through. The medical device 6 includes an expandable endo section 7, as shown in FIG. 8*b*, that can be compacted within a sheath 8 in order to be deployed inside a vessel such as the aorta 9. The sheath is splittable in order that the endo section 7 expands to engage the inner walls of the aorta.

Each of the sides 4, 5 has an arm member 10, at least a section of which can move radially inwardly and outwardly in relation to the longitudinal axis 11 of the sheath splitter. The arm members are provided with guide slots 12 at their proximal ends, through which the sheath material 8 can pass. In this regard, as shown particularly in FIGS. 1 and 2*b*, the sheath material runs along a sheath pathway up through the guide slot 12 on an inside face of the arm member 10 to the exterior of the apparatus and subsequently is directed distally along the exterior surface of the apparatus to a distal guide 13 at a distal end of the apparatus. In this embodiment, the exterior profile of each arm member includes a raised point 21 along the sheath pathway against which sheath material will engage when tensioned, to assist in urging the arm member inwardly towards the longitudinal axis 11, which results from the arm members in their natural position being wider than the outer profile of the sheath.

The arm members may be formed of material whereby they can deflect naturally due to the resilience of the material. Further, the profile of the arm members may be formed to promote flexibility at certain points, as shown at points 22 or mechanical articulated hinges 30 may be incorporated into the arm members as shown in the embodiment of FIG. 9. Furthermore, the neutral position of the arm members may be configured to be a closed or open position so that flexibility is only required in one direction. In this respect, as shown in FIG. 10, separate components such as a band 24 may be provided which constrain the arm members 10 in a closed position and which can be removed once the sheath has been split to allow the arm members 10 to open.

FIGS. 3 and 4*a* to 4*c* show the mechanism for attachment of the sheath splitter apparatus to the medical device delivery system. In this respect, the opposing sides 4,5 of the body 3 include respective clamp elements 14, 15 that are movable from an open position as shown in FIG. 4*a* to a closed position as shown in FIG. 4*c*. In this connection the body sides 4, 5 are hinged together by hinge 16 so that the sides 4,5 can be pivoted to allow the clamp elements to come together to close on a medical device that extends along the longitudinal axis 11 of the apparatus.

More specifically, the clamp elements 14,15 inter-engage on coupling of the body sections 4,5 to compress the material of a medical device provided in the apparatus.

In this regard, the clamp profile on each body section is tooth-like, and defines a central aperture 17 when the body sections are coupled, the central aperture being dimensioned for compressing the medical device sufficiently against its delivery shaft 26 to prevent blood leakage there-between, but loose enough to allow the medical device delivery shaft to slide within the medical device.

The clamp profiles of the clamp elements 14, 15 may be tooth-like with a pair of prongs 18 and a central spacing 19 such that when in a closed configuration, the central aperture 17 is established which is dimensioned suitably to clamp on the medical device.

Use of the splitter is described with reference to FIGS. 5*a*, 5*b*, 6*a*, 6*b*, 7 and 8*a* to 8*f*.

Figure 5A:
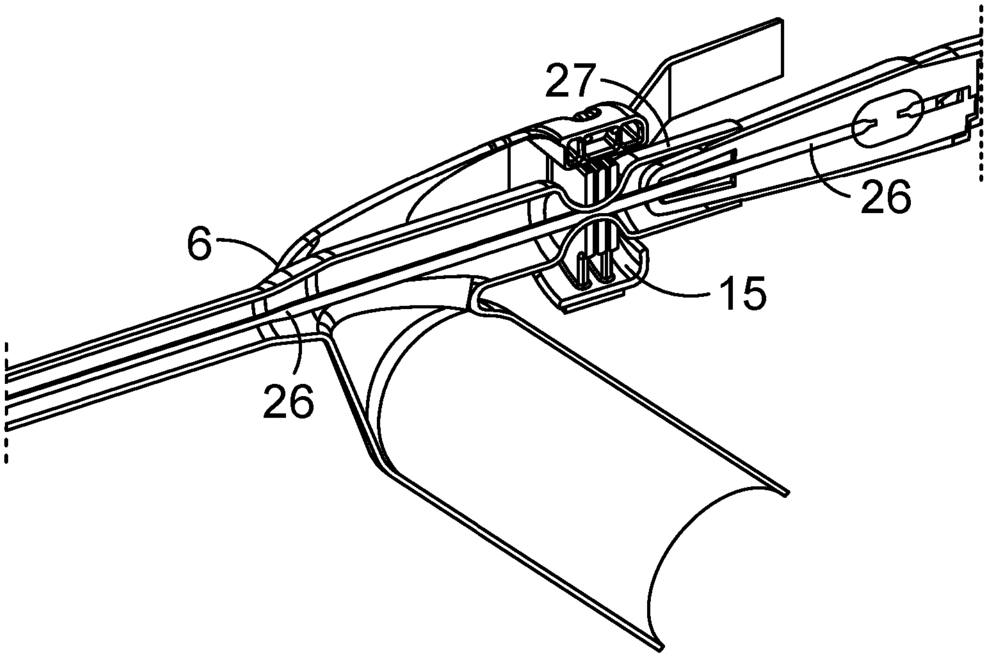
Figure 5B:
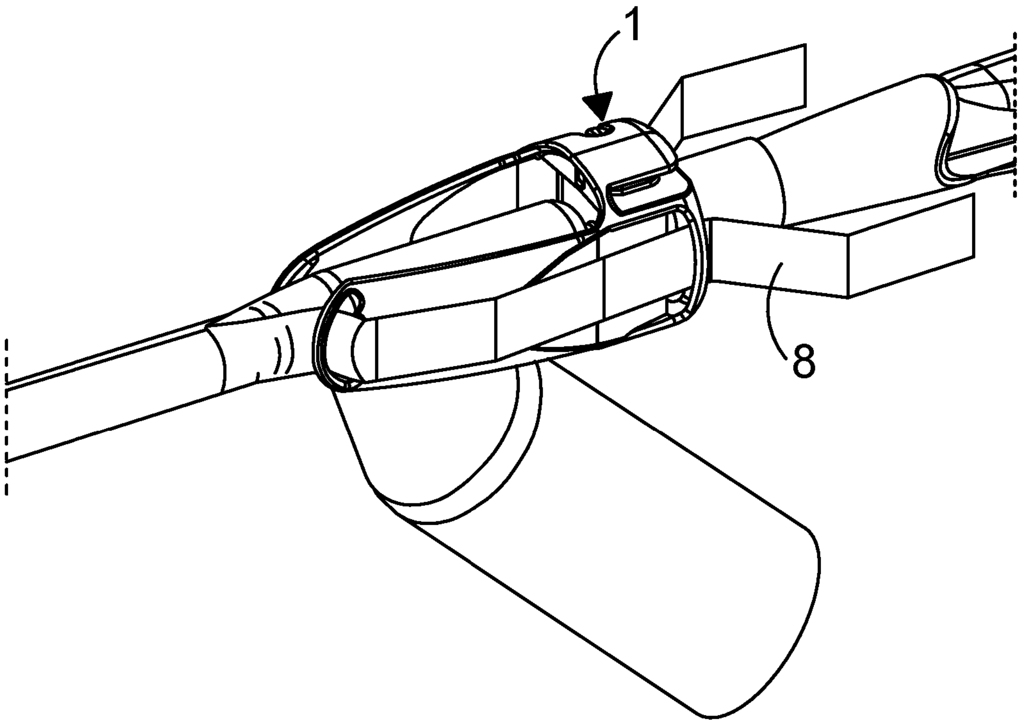

FIGS. 5*a* and 5*b* show a compacted and sheathed medical device 6, with the sheath splitting apparatus clamped onto an access branch 27 of the medical device. The cutaway view of FIG. 5*a* shows the clamp profile of clamp element 15 clamping the exterior of the medical device 6 against the delivery shaft 26 to prevent blood leakage there-between, but loose enough to allow the medical device delivery shaft 26 to slide within the medical device 6 at the clamping area.

Figure 6A:
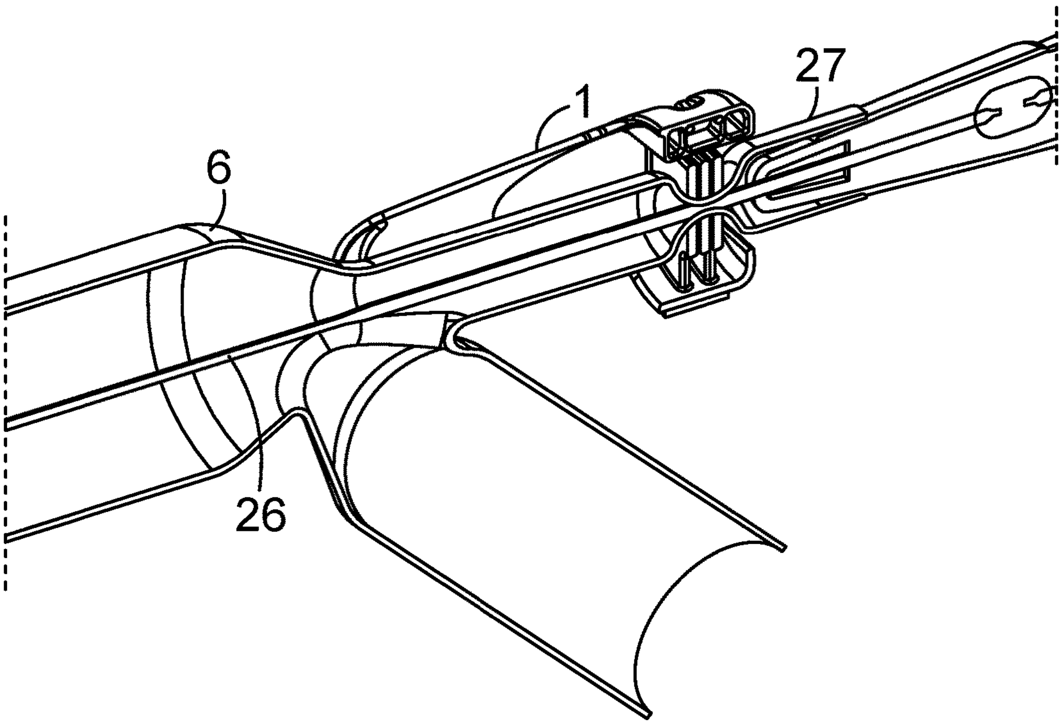
Figure 6B:
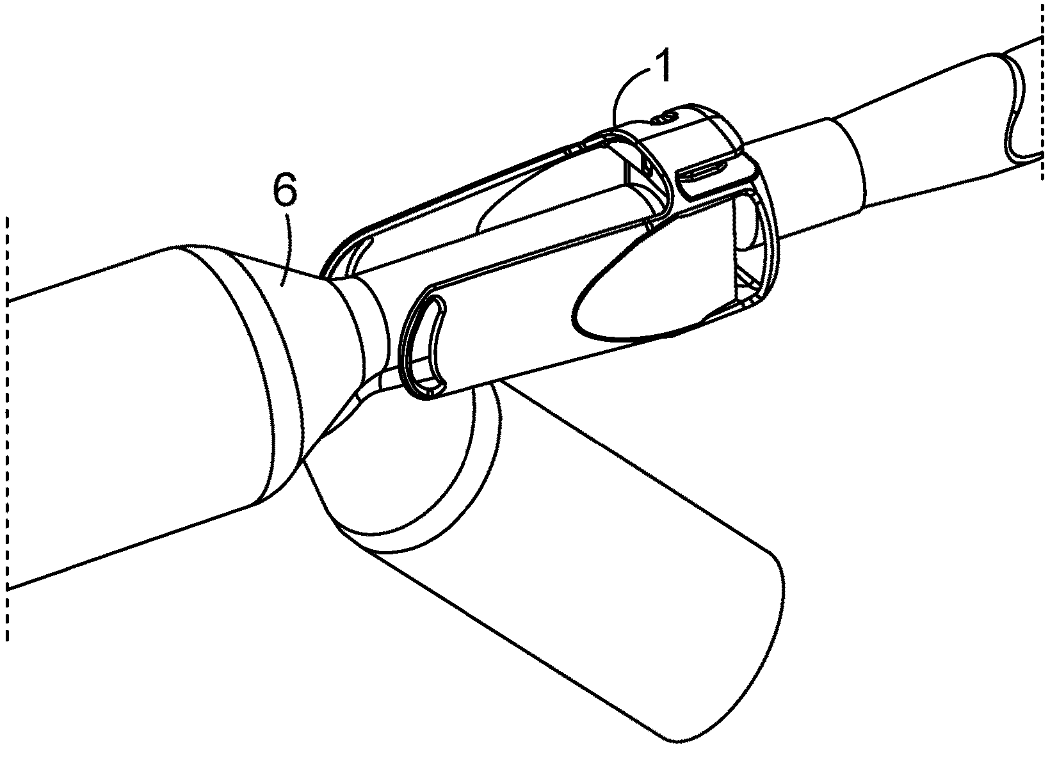

In FIGS. 6*a* and 6*b*, the medical device 6 is deployed with the sheath splitting apparatus still clamped on the access branch 27. The sheath material 8 has been removed allowing the medical device 6 to expand.

Figure 7:
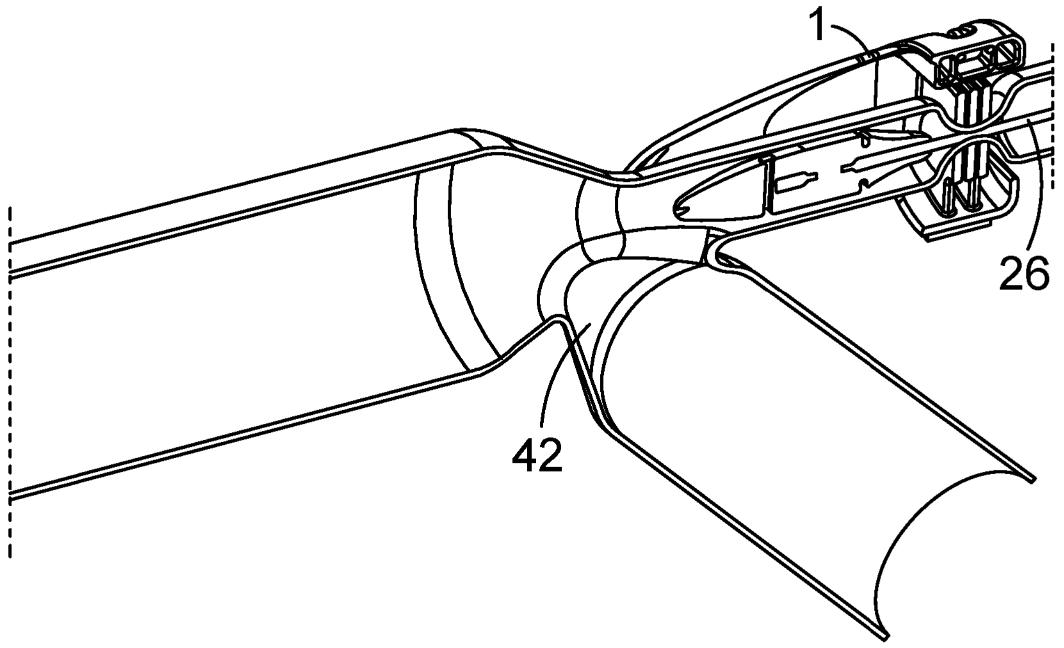

Then in FIG. 7, with the sheath splitting apparatus still clamped in position onto the access branch 27, components of the apparatus such as the delivery shaft 26 are retracted through the apparatus, past the junction 42 carrying blood flow.

Figure 8A:
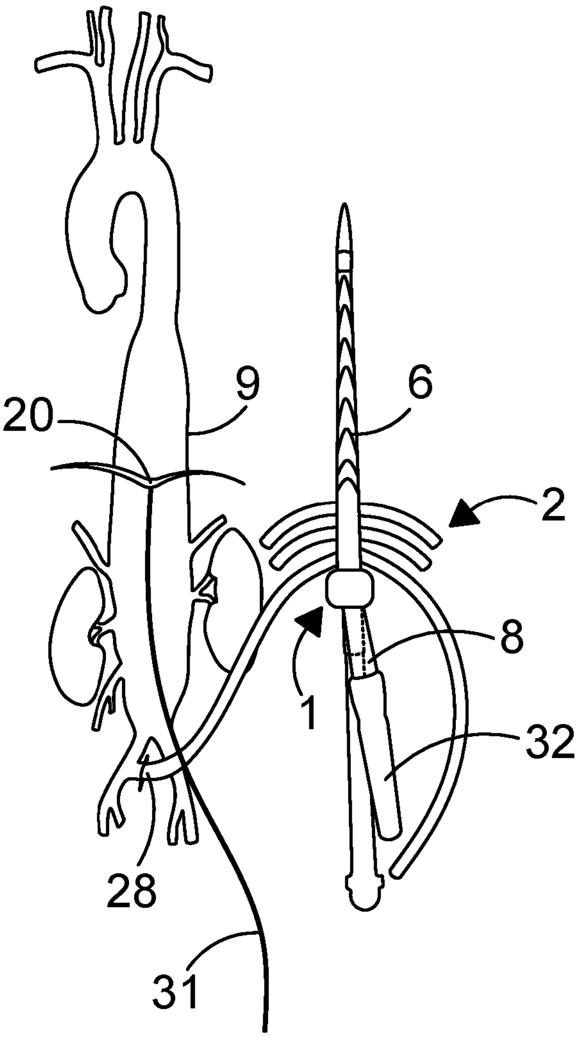
Figure 8B:
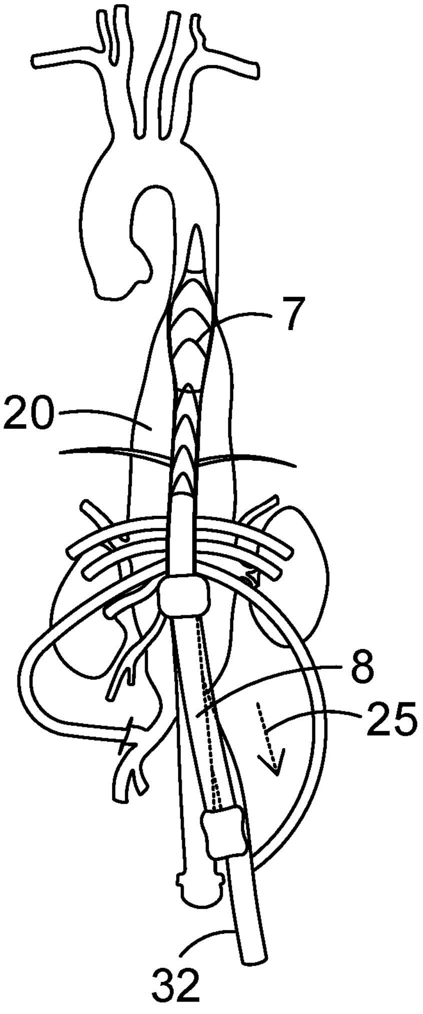

FIGS. 8*a* to 8*f* show use of the apparatus in the context of an aneurysm. As shown in FIG. 8*a*, the medical device 6 is provided at a proximal end of delivery system 2, with a sheath splitter apparatus 1 being provided at a distal end of the system. In a first step, an iliac component 28 of the device is attached to the patient and clamped. An incision is created in the aorta 20 which is then dilated over a guide wire 31.

In a second step shown in FIG. 8*b*, the device 6 is inserted over the guidewire 31 through the vessel wall and deployed. In order to deploy the device, the sheath material 8 encapsulating the medical device is removed distally in the direction as shown by arrow 25. In this connection, tails of the sheath material are thread along the sheath pathways along the sheath splitter and can be accessed and pulled rearwardly to deploy the device by pulling the sheath-pull handle 32.

Figure 8C:
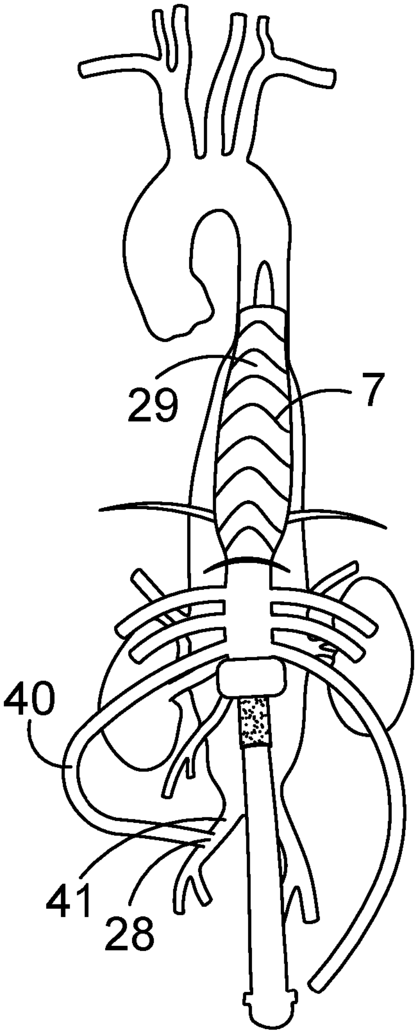

Then at a third step shown in FIG. 8*c*, the iliac component 28 is unclamped to allow blood to flow through the unsheathed device from proximal end 29 via the iliac branch 40 into the patient's iliac 41 and back into the aneurysm and perfuse the visceral vessels.

Figure 8D:
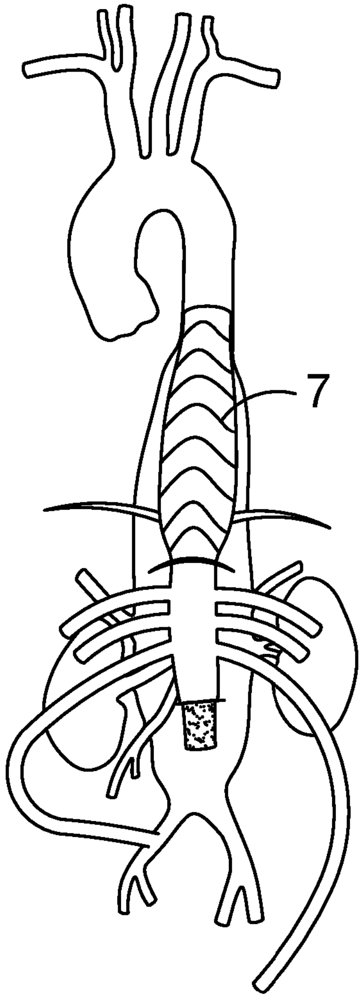

FIG. 8*d* shows the fourth step where the device is released and components of the delivery system are retracted through the splitter apparatus. In this regard, after the step shown in 8*c*, the device is released from attachment to the delivery system and the delivery system shaft/tip can be retracted relative to the clamping sheath splitter, to the position shown in FIG. 7. This then allows the access branch of the device to be clamped proximal to the sheath splitter/delivery system tip so that the delivery system (including sheath splitter) can be fully removed without any blood loss through the access branch. FIG. 8*d* shows the device, with clamped access branch, after removal of the delivery system.'

Figure 8E:
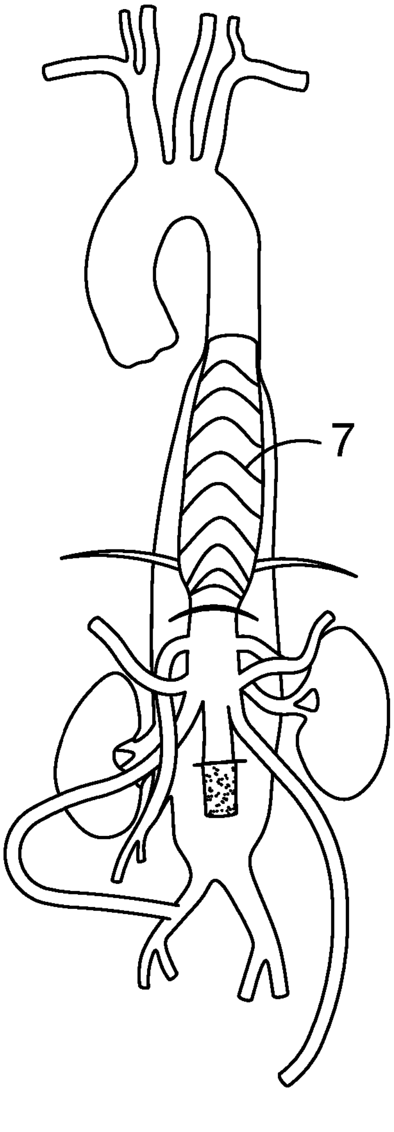

At FIG. 8*e*, the visceral vessels are debranched onto the medical devices with minimal ischemia.

Figure 8F:
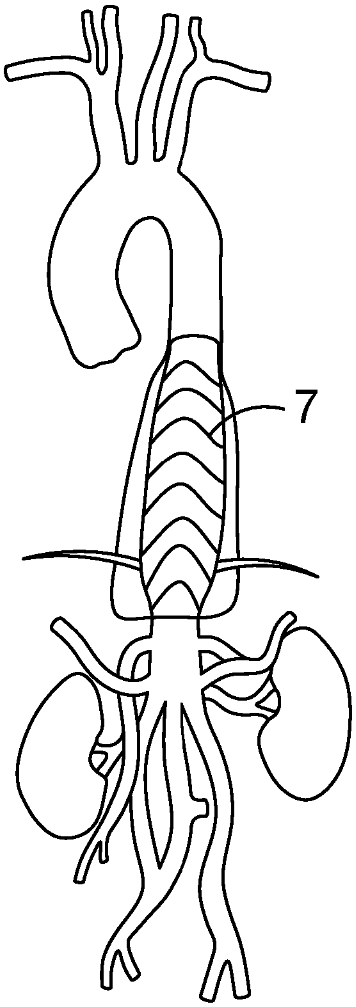

Then finally the 6$^{th}$ step shown in FIG. 8*f*, the aneurysm sac is removed.

In this connection, it will be appreciated that in an off-pump procedure, unsheathing an endovascular device will tend to cause it to fill with blood very quickly. The present invention provides a shape-changing haemostatic sheath splitter component that facilitates unsheathing of a quickly-pressurised medical device using flexible arm members 10 that control the force on the sheath as it splits and the device as it expands.

Meanwhile, blood loss is minimised by having clamp elements 14, 15 of the splitter at an appropriate position of the medical device that still enable a central delivery shaft 26 to be retracted substantially through a fitting gap 17 in the clamping element without blood loss.

In this connection, the sheath splitter 1 is assembled with one or more tails of the sheath (corresponding with the number of flexible arms and slots) passing through guide slots 12 from the inside of the arm member to the outside of the apparatus along a sheath pathway, and joined by a singular handle 32 nearest the operator; which, if pulled will:

1. cause the sheath 8 to withdraw and release the device until the sheath splits completely and is removed through the slots in the flexible arms using the attached handle; and
2. cause a controlled opposing force between the sheath tails splitting outwards and the arms flexing inwards, due to the configuration of the sheath tails through the guide slots of the arm members.

The flexible arm members 10 then provide a minimal opposing force for the pressurised device 6 to help prevent it from damage.

In this regard, the sheath splitter may comprise one or more of the following features:—

1. One or more arm members/elongated members 10, each with,
   a. a flexible joint 22;
   b. a fully or partially closed guide slot 12,13 that a sheath tail is weaved through;
2. a clasp/clamp attached to the arm members,
   a. which may ideally have two clamp elements 14, 15 such as plates, on one side, and one on the other that engages between the two of the first side to form a tri-layered clasp when the two sides are closed together;
   b. with a gap 17 at the centre formed by the shape of the tri-layer plates for the device and central shaft.

Once the sheath 8 is removed from the medical device 6, because it is being implanted 'off-pump', an endo section 7 will inflate with blood and eventually start to push against the splitter component. To mitigate risk of damage to the device associated with this interaction between the device and the splitter component, the splitter is configured so that it can change shape to accommodate the change in shape of the device. This mitigates the risk of the splitter causing any damage to the device while it is pressurised.

An additional feature which enables an 'off-pump' implantation is that the attachment of the sheath splitter to the delivery system is such as to prevent loss of blood through the splitter component. Moreover, the attachment allows for removal or retraction of the rest of the delivery system with minimal blood-loss, i.e. the shaft of the delivery system can slide through the splitter attachment so that the access branch (the branch on the device through which the delivery system is placed) can eventually be clamped proximal to the delivery system and then the splitter component removed.

The embodiment of the sheath splitter shown in the Figures has two elongated arm members 10, both of which end with a slot or window through which either half of the split sheath can pass. These slots do not split the sheath in a traditional manner, which would generally utilise a sharp cutting edge, but instead force the two separate ends of the sheath in opposing directions as they travel through the slots, forcing the sheath apart and causing it to split.

The geometry of the arm members ensure that they have a certain amount of built in flexibility and in their natural state they are approximately parallel to the main axis of the apparatus. When the sheath 8 is pulled through the splitter, the force applied to the splitter arms by the sheath causes the arm members to move closer together, bringing the slots more in-line with the start of the split on the sheath and thus facilitating the travel of the sheath through the splitter component. Once the sheath is removed and the device is inflated with blood, the pressure of the device against the splitter arm members forces them apart. This means that the innate flexibility of the arm members prevents them from restricting the size of, or applying excessive forces to, the device as it is pressurised.

With regard to the attachment of the splitter to the delivery system, as described above, with reference to FIGS. 3 and 4 in the preferred embodiment, it utilises a set of three features (two on one side of the splitter body and one on the opposite side), which overlap when the splitter is in its closed position. These essentially clamp the fabric of the device onto the delivery system shaft. This clamping effect is tight enough to prevent any blood from leaving the device through the branch, but is still loose enough to allow the shaft of the delivery system to slide through the clamped branch when required.

In the preferred embodiment, the sheath splitter 1 hence has two splitting elements, in the form of arm members (one for either side of the sheath) to facilitate the splitting of the sheath and then guiding of each split half of the sheath around the device, to prevent any damage that could be caused to the device by the movement of the sheath.

The splitting elements have sufficient flexibility to deflect inward during the splitting process but then deflect outward once the sheath is removed and the device increases in pressure/diameter.

The splitter also has the ability to be removed from the delivery system/device once its function has been completed in order to allow the rest of the deployment sequence to take place. This is currently achieved by locking the splitter together with a length of suture during manufacture/assembly, which is then cut during the procedure to allow the splitter to be opened up and removed from the delivery system.

Instead of using fully formed guide windows to guide the sheath ends apart, each guide could incorporate an open slot, essentially getting around the requirement of the guiding window to fully encapsulate the sheath.

Furthermore, instead of using two separate windows, the sheath could be split into any number of different segments, i.e. using one window to create a single split down one side of the sheath or using more than two windows to create multiple different sheath ends.

As shown in the embodiment of FIG. 10, the splitting elements' natural position could be in a substantially open configuration. This could further incorporate separate components 24 which essentially constrain the splitter in a closed position and then once the sheath has been split these additional components are removed, which then allows the splitter arms to open outwards.

In this regard, the splitting elements' natural position could equally be in a more closed position so that flexibility is only required in one direction (i.e. outwards).

This could also negate the requirement for built in flexibility in the part and could utilise something else, such as a hinge as shown in FIG. 9, to facilitate the movement of the splitting elements.

Instead of using overlapping features to clamp the splitter onto the delivery system, the apparatus could use compressive plates or a more compressible material in order to create a blood-tight attachment, such as rubber or silicone. Using some kind of compressive material or variable compressive force could allow for full removal of the delivery system through the component without the requirement to clamp the access branch.

For example, if the clamping force could be reduced in a controlled manner to allow the entire tip of the delivery system to be removed through the splitter but then subsequently reapplied to such an extent that blood cannot escape through the access branch, then the splitter could be left on the branch in lieu of using clamping forceps to prevent blood loss, until such a time as the branch is required for connecting to the native vessel.

Instead of using suture to lock the body of the sheath splitter halves together it could utilise a snap fit or removable bolt. This could also incorporate some mechanism that allows for temporary release of the clamping force, i.e. to allow for removal of the delivery system, but then having the ability to clamp back onto the branch to prevent blood loss once the delivery system has been removed. This would remove the requirement for a set of clamping forceps to prevent blood loss once the delivery system is removed from inside the branch.

Having the splitting arm member elements' natural position being roughly half way between fully opened and fully closed means that the natural flexibility of the chosen material should be suitable in both directions.

The invention claimed is:

1. A sheath splitting apparatus for use with a medical device delivery system for deploying a sheathed medical device; the sheath splitting apparatus comprising:

a) a body having a medical device pathway for receiving a medical device, the body defining a longitudinal axis and having opposing sides with a distal guide slot at each opposing side; and b) one or more arm members at a proximal end of the sheath splitting apparatus and at each opposing side of the body, each arm member having a proximal end and a distal end, and being movable inwardly and outwardly in relation to the medical device pathway, each arm member having a proximal guide slot at the proximal end of each arm, the proximal guide slot and distal guide slot defining a sheath pathway for guiding sheath material removed from the sheathed medical device to pass through the proximal guide slot and the distal guide slot, thereby causing tension on the sheath material to move the arm members.

2. The sheath splitting apparatus of claim 1, wherein two arm members are provided.

3. The sheath splitting apparatus of claim 1, wherein at least a section of each arm member is formed of resiliently deformable material.

4. The sheath splitting apparatus of claim 1, wherein at least a section of each arm member is hingeably mounted.

5. The sheath splitting apparatus of claim 1, wherein-said each arm member section deflects radially inwardly under the action of sheath material being pulled along the sheath pathway.

6. The sheath splitting apparatus of claim 1, wherein a proximal end of each arm member naturally extends to a position radially outwardly from a medical device within the apparatus.

7. The sheath splitting apparatus of claim 1, wherein each arm member at its proximal end presents a profile accommodating outward deflection of the arm member on distally directed flow through a medical device present in the apparatus.

8. The sheath splitting apparatus of claim 7, wherein each arm member has a curved profile at its proximal end.

9. The sheath splitting apparatus of claim 1, wherein each arm member extends longitudinally, substantially parallel with the axis of the medical device pathway.

10. The sheath splitting apparatus of claim 1, wherein the distal guide slot is circumferentially aligned with the proximal guide slot.

11. The sheath splitting apparatus of claim 10, wherein the proximal and distal guide slots are provided on either side of a hinge point of each arm member.

12. The sheath splitting apparatus of claim 1, wherein the sheath pathway extends from inside each arm member, through the proximal guide slot to the exterior of the arm member, along the exterior of the arm member and through the distal guide slot provided distally of the proximal guide slot.

13. The sheath splitting apparatus of claim 1, wherein the body has clamping means for reducing the cross-sectional area of the medical device pathway.

14. The sheath splitting apparatus of claim 13, wherein the clamping means defines a central aperture dimensioned for compressing the medical device sufficiently against a delivery shaft to prevent blood leakage there-between, but loose enough to allow the delivery shaft to slide within the medical device.

15. The sheath splitting apparatus of claim 1, wherein the body comprises a plurality of body sections couplable together for housing around said medical device to be delivered.

16. The sheath splitting apparatus of claim 15, wherein said body has two body sections that are hingeably couplable.

17. The sheath splitting apparatus of claim 15, wherein each body section carries a clamp profile, the clamp profiles of the body sections inter-engaging on coupling of the body sections for compressing the material of a medical device present in the apparatus.

18. The sheath splitting apparatus of claim 17, wherein the clamp profile on each body section is tooth-like, and defines a central aperture when the body sections are coupled, the central aperture being dimensioned for compressing the medical device sufficiently against a delivery shaft to prevent blood leakage there-between, but loose enough to allow the delivery shaft to slide within the medical device.

19. The sheath splitting apparatus of claim 18, wherein the clamp profile on one body section has a single tooth profile and the inter-engaging profile on the other body section has a pair of tooth profiles, that slidably interlock when the body sections are coupled together.

20. A medical device delivery system for deploying a sheathed medical device, the system comprising:

a) a medical device delivery shaft for holding a deployable medical device;

b) a sheathed medical device provided on said delivery shaft; and c) a sheath splitting apparatus including a body having a medical device pathway for receiving said medical device provided on said delivery shaft, the sheath splitting apparatus comprising one or more arm members, being movable inwardly and outwardly in relation to the medical device pathway, each arm member having a distal guide slot at the distal end and proximal guide slot at the proximal end of each arm defining a sheath pathway for guiding sheath material removed from the sheathed medical device through the proximal guide slot and the distal guide slot, thereby causing tension on the sheath material to move the arm members.

21. The medical device delivery system of claim 20, wherein each arm member is configured to deflect radially inwardly on sheath removal towards said delivery shaft and then radially outwardly post sheath removal.

22. The medical device delivery system of claim 20, wherein the sheath splitting apparatus comprises clamping means configured to compress the medical device against the delivery shaft to prevent blood leakage.

* * * * *